United States Patent
Rudman et al.

(10) Patent No.: US 9,949,671 B2
(45) Date of Patent: Apr. 24, 2018

(54) DIAGNOSTIC MOUTHPIECES

(71) Applicant: ORTHOACCEL TECHNOLOGIES INC., Bellaire, TX (US)

(72) Inventors: Robert T. Rudman, Bellaire, TX (US); Michael K. Lowe, Bellaire, TX (US); David W. Ward, Bellaire, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 757 days.

(21) Appl. No.: 14/329,268

(22) Filed: Jul. 11, 2014

(65) Prior Publication Data

US 2014/0322661 A1    Oct. 30, 2014
US 2017/0181675 A9    Jun. 29, 2017

Related U.S. Application Data

(60) Provisional application No. 61/857,089, filed on Jul. 22, 2013, provisional application No. 61/870,534, filed on Aug. 27, 2013.

(51) Int. Cl.
*A61B 5/145*    (2006.01)
*A61C 7/00*    (2006.01)
*A61C 7/08*    (2006.01)

(52) U.S. Cl.
CPC .......... *A61B 5/14507* (2013.01); *A61C 7/008* (2013.01); *A61C 7/08* (2013.01)

(58) Field of Classification Search
CPC ......... A61C 7/008; A61C 7/08; G01N 33/558
See application file for complete search history.

(56) References Cited

U.S. PATENT DOCUMENTS

| | | | |
|---|---|---|---|
| 5,770,460 A | 6/1998 | Pawlak et al. | |
| 5,798,273 A | 8/1998 | Shuler et al. | |
| 6,063,588 A | 5/2000 | Lamster | |
| 6,372,513 B1 | 4/2002 | Nguyen | |
| 6,399,295 B1 | 6/2002 | Kaylor et al. | |
| 6,648,639 B2 | 11/2003 | Mao | |
| 6,656,744 B2 | 12/2003 | Pronovost | |
| 6,832,912 B2 | 12/2004 | Mao | |
| 7,029,276 B2 | 4/2006 | Mao | |
| 7,344,893 B2 | 3/2008 | Kirkegaard | |
| 7,605,004 B2 | 10/2009 | Zhou | |
| 8,377,643 B2 | 2/2013 | Mehra | |
| 8,377,710 B2 | 2/2013 | Whitesides | |
| 2002/0155029 A1* | 10/2002 | Mink ................. | A61B 10/0051 422/412 |

(Continued)

FOREIGN PATENT DOCUMENTS

WO    1998029746    7/1998

OTHER PUBLICATIONS

Kau, et al., The clinical evaluation of a novel cyclical force generating device in orthodontics, Orthodontic Practice 1(1) (2010).

(Continued)

*Primary Examiner* — Michael C Stout
*Assistant Examiner* — Nicholas E Kolderman
(74) *Attorney, Agent, or Firm* — Boulware & Valoir

(57) ABSTRACT

Diagnostic mouthpieces and separate pads for same allow dental devices of various types to have a dual purpose. The diagnostic mouthpieces allow frequent use and early intervention.

3 Claims, 18 Drawing Sheets

(56) References Cited

U.S. PATENT DOCUMENTS

| | | | |
|---|---|---|---|
| 2005/0181517 A1* | 8/2005 | Chandler | B01L 3/5023 436/169 |
| 2008/0119698 A1* | 5/2008 | Tricca | A61B 5/0088 600/309 |
| 2008/0183101 A1 | 7/2008 | Richard | |
| 2008/0227046 A1* | 9/2008 | Lowe | A61C 7/00 433/2 |
| 2008/0227047 A1 | 9/2008 | Lowe | |
| 2009/0047667 A1 | 2/2009 | Wong | |
| 2010/0055634 A1* | 3/2010 | Spaulding | A61C 7/00 433/5 |
| 2010/0196941 A1 | 8/2010 | Braun | |
| 2010/0210023 A1 | 8/2010 | Wong | |
| 2010/0233742 A1 | 9/2010 | Fujinaka | |
| 2011/0236314 A1 | 9/2011 | Teo | |
| 2012/0021375 A1* | 1/2012 | Binner | A61B 5/097 433/89 |
| 2012/0028261 A1 | 2/2012 | Trivedi | |
| 2012/0040300 A1 | 2/2012 | Levens | |
| 2012/0172677 A1* | 7/2012 | Logan | A61B 5/082 600/301 |
| 2012/0276546 A1 | 11/2012 | Souno | |
| 2012/0322018 A1 | 12/2012 | Lowe | |
| 2012/0322086 A1 | 12/2012 | Gamier | |
| 2013/0017559 A1 | 1/2013 | Babu | |
| 2013/0022961 A1 | 1/2013 | Gorelik | |
| 2013/0022969 A1 | 1/2013 | Kim | |
| 2013/0059263 A1 | 3/2013 | Lowe | |
| 2013/0065769 A1 | 3/2013 | Wong | |
| 2013/0309656 A1* | 11/2013 | Davis | G01N 21/8483 435/5 |

OTHER PUBLICATIONS

Kaufman, E., et al., The Diagnostic Applications of Saliva—A Review, Crit. Rev. Oral Biol. Med 13(2) 2002.

Bretz W.A., et al., Systemic inflammatory markers, periodontal diseases, and periodontal infections in an elderly population, J Am Geriatr Soc. 53(9):1532-7 (2005).

Norlund A., et al., Improved ability of biological and previous caries multimarkers to predict caries disease as revealed by multivariate PLS modelling, BMC Oral Health 9:28 (2009).

Pederson A.N.M., et al., Salivary changes and dental caries as potential oral markers of autoimmune salivary gland dysfunction in primary Sjögren's syndrome, BMC Clinical Pathology 5:4 1472-6890-5-4 (2005).

Rathnayake N., et al., Salivary Biomarkers for Detection of Systemic Diseases, PLoS One. 8(4) (2013).

Ruhl S., The scientific exploration of saliva in the post-proteomic era: from database back to basic function, Expert Rev Proteomics. 9(1):85-96 (2012).

Soo-Quee Koh D., et al., The use of salivary biomarkers in occupational and environmental medicine, Occup Environ Med. 64(3): 202-210 (2007).

Hart, T.C., Identification of Microbial and Proteomic Biomarkers in Early Childhood Caries, Intl. J. Dentistry 2011, Article ID 196721, (2011).

* cited by examiner

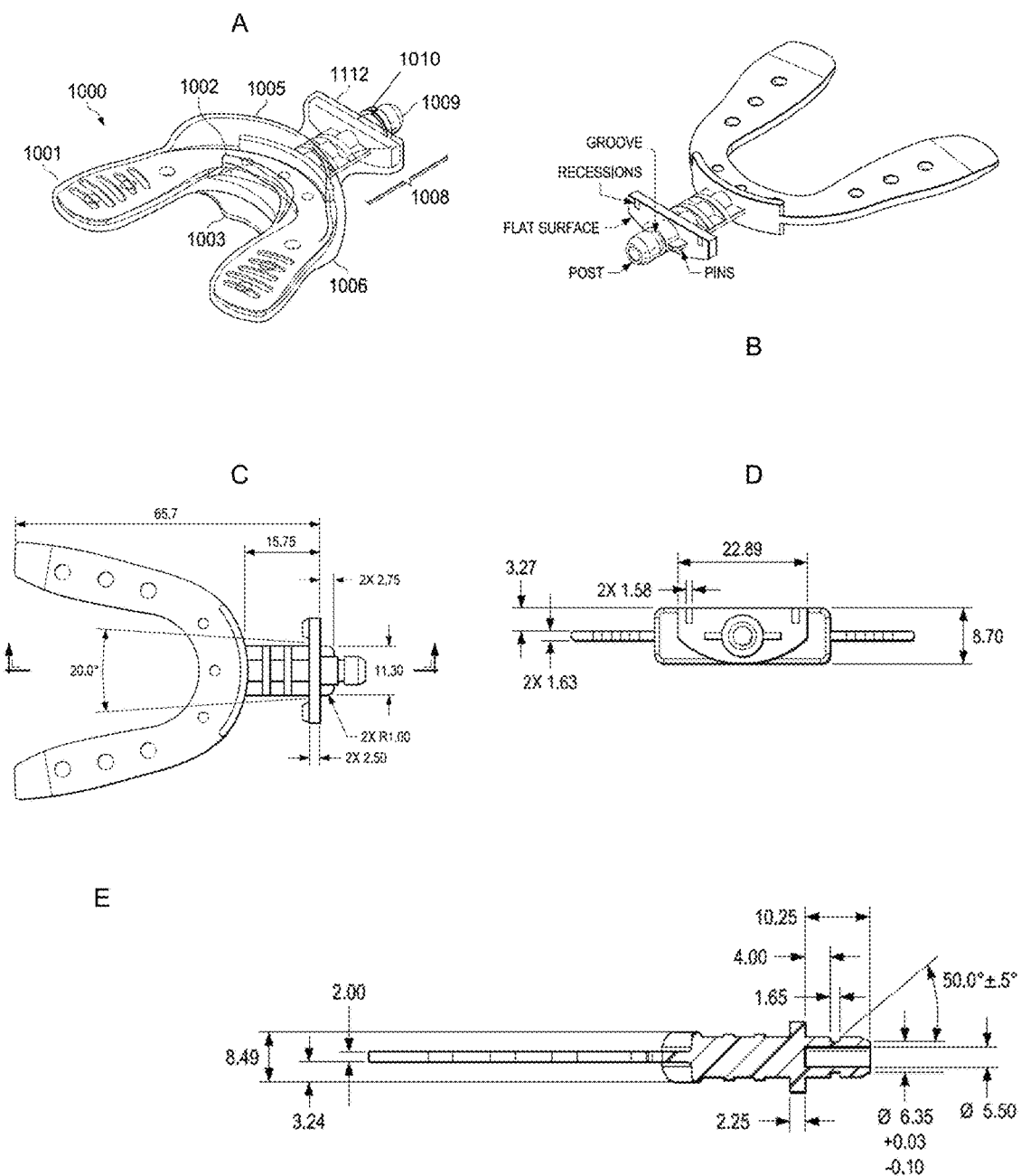
FIGURE 6A-E (Prior Art)

FIGURE 7 (Prior Art)

| Table 1: Salimetric® multistep assay kits for salivary biomarkers | | | | | |
|---|---|---|---|---|---|
| Kit number | Target Analyte | Serum-Saliva Correlation | Sensitivity | Salivary Test Volume | Collection Volume |
| 1-2602 | 17α-Hydroxyprogesterone | 0.64 | 3 pg/mL | 50 μL | 125 μL* |
| 1-1902 | Alpha-Amylase | - | N/A | 10 μL of saliva then 8 μL of X200 dilution | 25 μL* |
| 1-2902 | Androstenedione | 0.77 | 5 pg/mL | 50 μL | 125 μL* |
| 1-3302 | C-Reactive Protein | - | 10 pg/mL | 15 μL of saliva then 50 μL of X10 dilution | 125 μL* |
| 1-3002 | Cortisol | 0.91 | <0.003 ug/dL | 25 μL | 75 μL* |
| 1-2002 | Cotinine | - | 0.15 ng/mL | 20 μL | 75 μL* |
| 1-1202 | DHEA | 0.86 | 5 pg/mL | 50 μL | 125 μL* |
| 1-1252 | DHEA-S | - | 43 pg/mL | 100 μL | 225 μL* |
| 1-3702 | Estradiol | 0.80 | 0.1 pg/mL | 100 μL | 225 μL* |
| 1-1802 (High Sensitivity) | Estriol | 0.87 | 1 pg/mL | 100 μL of X2 dilution | 175 μL* |
| 1-1802 | Estriol | 0.87 | 16 pg/mL | 25 μL | 75 μL* |
| 1-3202 | Estrone | - | 1 pg/mL | 100 μL | 225 μL* |
| 1-3902 | Interleukin-1 Beta | - | <0.37 pg/mL | 20 μL | 50 μL* |
| 1-3402 | Melatonin | 0.81 | 0.58 pg/mL (LOD) | 100 μL | 225 μL* |
| 1-1502 | Progesterone | 0.87 | 5 pg/mL | 50 μL | 125 μL* |
| 1-1602 | Secretory Immunoglobulin A | - | 2.5 μg/mL | 25 μL | 50 μL* |
| 1-2402 | Testosterone | 0.96 | 1 pg/mL | 25 μL | 75 μL* |
| 1-1302 | Transferrin & Blood Contamination | - | 0.08 mg/dL | 20 μL | 75 μL* |

FIGURE 8 (Prior Art)

| Table 2 Comparative blood and saliva levels of selected biomarkers, from Soo (2007) | | |
|---|---|---|
| Biomarker | Normal range | |
| | Blood | Saliva |
| Cortisol | 2–25 mg/dl (serum) | 3.5–27.0 mg/dl |
| Morning range | 7–25 mg/dl | 2.0–4.5 mg/dl |
| Evening range | 2–25 mg/dl | 1.0–3.0 mg/dl |
| Chromogranin A | 20–30 ng/ml (serum) | 0.30–0.45 pmol/mg protein |
| α-Amylase | 0.05–0.125 U/ml (serum) | 19–308 U/ml |
| Secretory IgA | – | Concentration: 100–900 µg/ml |
| | | Secretion rate: 5–150 µg/min |
| Lysozyme | 1–15 µg/ml (serum) | Concentration: 10–300 µg/ml |
| | | Secretion rate: 3–120 µg/min |
| Lead | 5–15 µg/dl (whole blood) | 0.7–7.5 µg/dl (15–50% of whole blood lead) |
| Cotinine (non-smokers) | <10 ng/ml (serum) | <10 ng/ml (10–40% higher than blood) |

FIGURE 9A (Prior Art)

Table 3a: Concentrations (mean and SD) for heart disease biomarkers in samples of stimulated saliva from 441 subjects.
p1 indicates significance of the differences after a bivariate comparison
p2 indicates the significance after compensation for differences in gender, age and smoking habits.
From Rathnayake (2013)

| Biomarker | Heart disease | p1 | p2 | Heart surgery | p1 | p2 | Hypertension | p1 | p2 |
|---|---|---|---|---|---|---|---|---|---|
| | Yes - 35 | | | Yes - 11 | | | Yes - 76 | | |
| | No - 406 | | | No - 430 | | | No - 365 | | |
| | Mean±SD | | | Mean±SD | | | Mean±SD | | |
| IL-1β(pg/ml) | 88.8±180.8 | 0.454 | 0.739 | 40.4±68.2 | 0.324 | 0.126 | 94.5 ±165.8 | 0.103 | 0.904 |
| | 73.5±109.4 | | | 75.6±117.4 | | | 70.6±103.1 | | |
| IL-6(pg/ml) | 6.7±8.1 | 0.525 | 0.528 | 7.0±4.5 | 0.779 | 0.775 | 7.8±13.1 | 0.905 | 0.983 |
| | 8.0±11.8 | | | 7.9±11.6 | | | 7.9±11.1 | | |
| IL-8(pg/ml) | 516.9±582.6 | 0.912 | 0.315 | 340.0±370.9 | 0.438 | 0.130 | 570.0±781.4 | 0.374 | 0.241 |
| | 503.1±719.8 | | | 508.4±715.7 | | | 490.5±693.8 | | |
| MMP-8(ng/ml) | 373.8±355.7 | 0.065 | 0.573 | 472.9±570.3 | 0.024 | 0.040 | 370.6±386.1 | 0.006 | 0.414 |
| | 287.2±256.4 | | | 289.5±253.4 | | | 278.1±231.2 | | |
| TIMP-1(ng/ml) | 231.6±153.9 | 0.126 | 0.265 | 289.2±209.8 | 0.656 | 0.671 | 238.0±176.6 | 0.208 | 0.132 |
| | 266.2±196.8 | | | 262.8±193.6 | | | 268.8±197.0 | | |
| MMP-8/TIMP-1 | 0.76±1.24 | 0.143 | 0.977 | 0.55±0.77 | 0.972 | 0.758 | 0.78±1.16 | 0.012 | 0.828 |
| | 0.54±0.81 | | | 0.56±0.86 | | | 0.51±0.77 | | |
| Lysozyme(ng/ml) | 373.4±462.3 | 0.748 | 0.411 | 522.3±745.4 | 0.319 | 0.126 | 307.3±325.4 | 0.047 | 0.566 |
| | 397.6±423.3 | | | 392.5±415.6 | | | 414.1±442.2 | | |
| Total protein concentration(ug/ml) | 847.9±408.6 | 0.703 | 0.780 | 807.6±499.2 | 0.914 | 0.761 | 876.8±481.9 | 0.215 | 0.913 |
| | 819.1±430.0 | | | 821.7±426.6 | | | 809.9±415.6 | | |

FIGURE 9B (Prior Art)

Table 3b Concentrations (mean and SD) for diabetes biomarkers in samples of stimulated saliva from 441 subjects.

| Biomarker | Diabetes | $p1$ | $p2$ | Bowel diseases | $p1$ | $p2$ | Muscle/joint diseases | $p1$ | $p2$ |
|---|---|---|---|---|---|---|---|---|---|
| | Yes - 16 | | | Yes - 31 | | | Yes - 102 | | |
| | No - 425 | | | No - 410 | | | No - 339 | | |
| | Mean±SD | | | Mean±SD | | | Mean±SD | | |
| IL-1β(pg/ml) | 65.0±80.6 | 0.636 | 0.399 | 87.5±103.6 | 0.526 | 0.712 | 101.2±154.1 | 0.008 | 0.017 |
| | 75.0±117.7 | | | 73.7±117.5 | | | 66.7±101.5 | | |
| IL-6(pg/ml) | 8.2±6.1 | 0.930 | 0.805 | 8.9±10.2 | 0.603 | 0.471 | 7.9±11.2 | 1.000 | 0.686 |
| | 7.9±11.6 | | | 7.8±11.5 | | | 7.9±11.5 | | |
| IL-8(pg/ml) | 583.8±538.0 | 0.876 | 0.872 | 922.2±1598.3 | 0.001 | 0.008 | 634.3±866.2 | 0.034 | 0.159 |
| | 501.2±715.3 | | | 472.6±582.8 | | | 465.1±651.3 | | |
| MMP-8(ng/ml) | 480.6±402.3 | 0.075 | 0.021 | 297.1±216.6 | 0.948 | 0.799 | 356.3±331.2 | 0.007 | 0.035 |
| | 287.0±257.7 | | | 293.8±269.8 | | | 275.3±240.7 | | |
| TIMP-1(ng/ml) | 193.9±209.9 | 0.195 | 0.152 | 286.0±231.2 | 0.503 | 0.461 | 279.5±213.0 | 0.341 | 0.262 |
| | 266.1±192.9 | | | 261.8±190.9 | | | 258.6±187.7 | | |
| MMP-8/TIMP-1 | 1.76±2.45 | 0.060 | 0.001 | 0.44±0.39 | 0.411 | 0.160 | 0.77±1.40 | 0.005 | 0.047 |
| | 0.52±0.70 | | | 0.57±0.88 | | | 0.50±0.59 | | |
| Lysozyme(ng/ml) | 337.6±172.3 | 0.221 | 0.747 | 451.5±516.4 | 0.451 | 0.174 | 336.7±264.9 | 0.111 | 0.949 |
| | 397.9±432.6 | | | 391.5±418.8 | | | 413.5±462.5 | | |
| Total protein concentration(ug/ml) | 866.8±235.3 | 0.459 | 0.958 | 1044.4±715.1 | 0.003 | 0.004 | 900.5 ± 491.0 | 0.033 | 0.113 |
| | 819.7±433.6 | | | 804.5±394.2 | | | 797.6 ± 405.8 | | |

FIGURE 9C (Prior Art)

Table 3c Concentrations (mean and SD) for tumor biomarkers in samples of stimulated saliva from 441 subjects

| Biomarker | Tumor | | | Mental illness | | | Inflammation | | |
|---|---|---|---|---|---|---|---|---|---|
| | Yes - 16 / No - 425 Mean±SD | p1 | p2 | Yes - 26 / No - 415 Mean±SD | p1 | p2 | Yes - 181 / No - 260 Mean±SD | p1 | p2 |
| IL-1β(pg/ml) | 133.8±199.3 / 72.4±112.0 | 0.038 | 0.204 | 62.3±103.9 / 75.5±117.3 | 0.576 | 0.839 | 84.5±129.0 / 67.9±106.8 | 0.142 | 0.873 |
| IL-6(pg/ml) | 12.8±20.7 / 7.7±10.9 | 0.081 | 0.077 | 5.1±5.6 / 8.1±11.7 | 0.196 | 0.243 | 7.9±11.0 / 7.9±11.7 | 0.966 | 0.593 |
| IL-8(pg/ml) | 1137.4±1539.6 / 480.4±650.1 | 0.001 | 0.005 | 352.2±336.7 / 513.7±725.3 | 0.261 | 0.439 | 605.5±901.3 / 435.0±531.5 | 0.013 | 0.478 |
| MMP-8(ng/ml) | 348.1±300.2 / 292.0±265.0 | 0.409 | 0.886 | 235.3±218.5 / 297.7±268.7 | 0.247 | 0.244 | 344.0±314.6 / 260.0±221.5 | 0.001 | 0.070 |
| TIMP-1(ng/ml) | 295.9±207.0 / 262.3±193.4 | 0.497 | 0.318 | 277.4±220.6 / 262.6±192.3 | 0.707 | 0.708 | 273.1±208.5 / 256.9±183.2 | 0.388 | 0.310 |
| MMP-8/TIMP-1 | 0.61±0.85 / 0.56±0.86 | 0.820 | 0.483 | 0.42±0.49 / 0.57±0.87 | 0.396 | 0.320 | 0.68±1.13 / 0.48±0.59 | 0.015 | 0.673 |
| Lysozyme(ng/ml) | 412.3±357.7 / 395.1±428.7 | 0.874 | 0.242 | 405.8±543.1 / 395.1±418.4 | 0.901 | 0.687 | 345.9±352.2 / 429.7±467.4 | 0.042 | 0.901 |
| Total protein concentration(ug/ml) | 970.6±492.3 / 815.7±424.9 | 0.156 | 0.358 | 832.2±489.0 / 820.7±424.5 | 0.894 | 0.809 | 895.8±510.0 / 770.5±353.4 | 0.002 | 0.026 |

FIGURE 10 (Prior Art)

Table 4: pH Indicator dyes

| Indicator | Low pH color | Transition pH range | High pH color |
|---|---|---|---|
| Gentian violet (Methyl violet 10B) | yellow | 0.0–2.0 | blue-violet |
| Malachite green (first transition) | yellow | 0.0–2.0 | green |
| Malachite green (second transition) | green | 11.6–14 | colorless |
| Thymol blue (first transition) | red | 1.2–2.8 | yellow |
| Thymol blue (second transition) | yellow | 8.0–9.6 | blue |
| Methyl yellow | red | 2.9–4.0 | yellow |
| Bromophenol blue | yellow | 3.0–4.6 | purple |
| Congo red | blue-violet | 3.0–5.0 | red |
| Methyl orange | red | 3.1–4.4 | yellow |
| Screened methyl orange (first transition) | red | 0.0–3.2 | grey |
| Screened methyl orange (second transition) | grey | 3.2–4.2 | green |
| Bromocresol green | yellow | 3.8–5.4 | blue |
| Methyl red | red | 4.4–6.2 | yellow |
| Azolitmin | red | 4.5–8.3 | blue |
| Bromocresol purple | yellow | 5.2–6.8 | purple |
| Bromothymol blue | yellow | 6.0–7.6 | blue |
| Phenol red | yellow | 6.4–8.0 | red |
| Neutral red | red | 6.8–8.0 | yellow |
| Naphtholphthalein | colorless to reddish | 7.3–8.7 | greenish to blue |
| Cresol Red | yellow | 7.2–8.8 | reddish-purple |
| Phenolphthalein | colorless | 8.3–10.0 | fuchsia |
| Thymolphthalein | colorless | 9.3–10.5 | blue |
| Alizarine Yellow R | yellow | 10.2–12.0 | red |

FIGURE 12 (Prior Art)

| Proteomic Biomarkers | | | Genomic Biomarkers | Microbial biomarkers | Other markers |
|---|---|---|---|---|---|
| Immunoglubilins | Calprotectin | Kininase | Cathepsin C gene Mutation | Aggregatibacter Actinomycetemcomitans | Calcium |
| Acid phosphatase | Caprylate esteraselipase | Lactoferrin | Collagen gene mutation | Campylobacter rectus | Cortisol |
| Alkaline phosphatase | Cathepsin B | Lactotransferrin | IL-1 polymorphisms | Mycoplasmas | Hydrogen sulfide |
| Aspartate Aminotransferase | CD14 | Lactate dehydrogenase | IL-10 polymorphisms | Porphyromonas Gingivalis | Methyl mercaptan |
| Aminopeptidases | Cystatins | Lysozyme | TNF Polymorphisms | Prevotella intermedia | Picolines |
| Beta-galactosidase | Elastase | MMP 1, MMP 2, MMP 3 | | Peptostreptococcus Micros | PMNs |
| Beta-glucosidase | Epidermal growth Factor | MMP-8, MMP-9 MMP-13 | | Prevotella nigrescens | Pyridine |
| Beta-glucuronidase | Esterase | ICTP | | Treponema denticola | |
| CRP | Fibronectin | Myeloperoxidase | | Tannerella forsythia | |
| Alpha-glucosidase | Gelatinase | Osteocalcin | | Treponema socranskii | |
| Histatin | Kallikrein | Osteonectin | | | |
| Mucins | Peroxidase | Osteopontin | | | |

FIGURE 13(Prior Art)

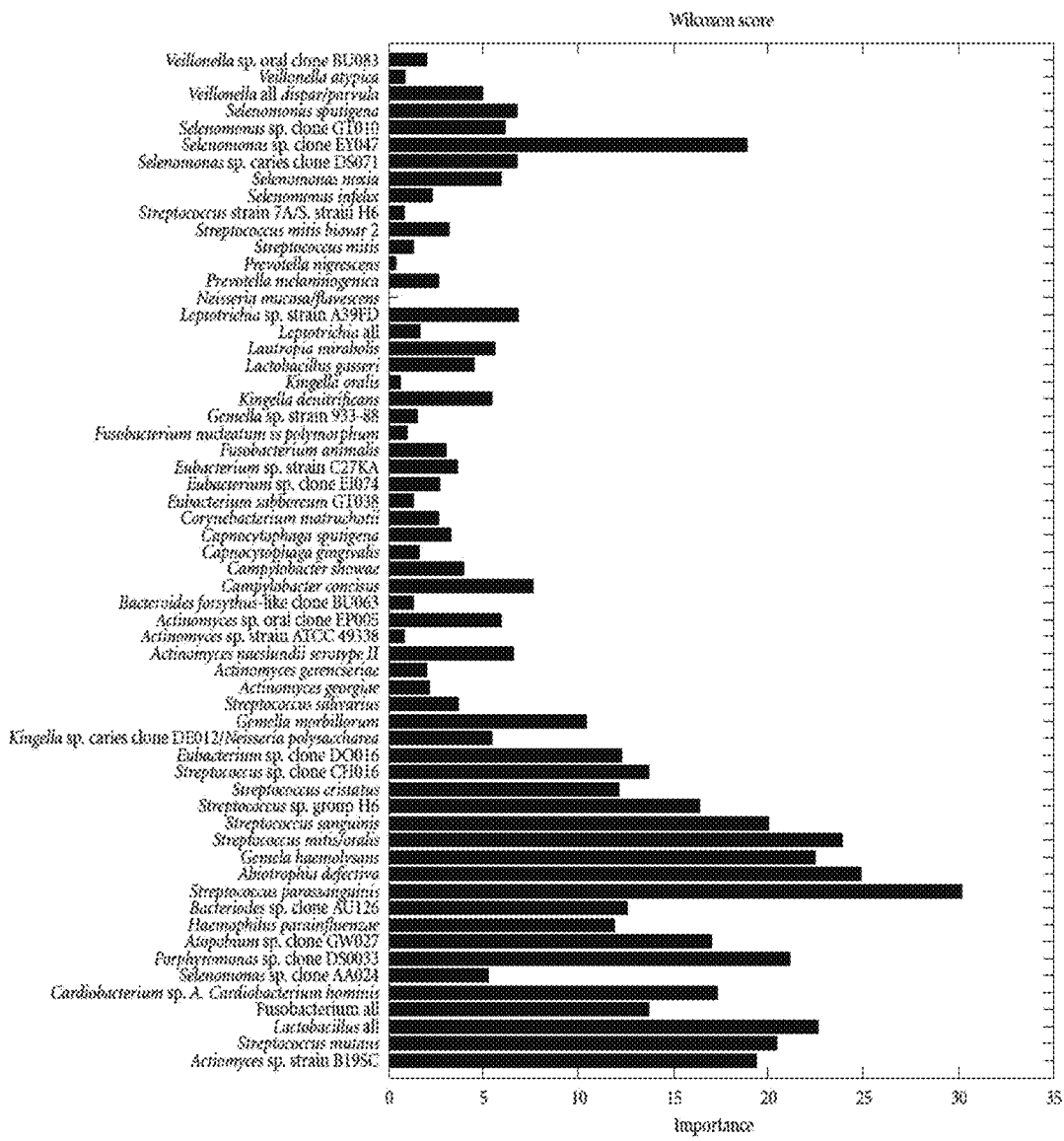

FIGURE 2: Importance of bacteria probes according to their individual discriminative power. Species of bacterial species or group are indicated along the y-axis. Shaded bars indicate the importance of the species as measured by the Wilcoxon rank-sum score (the score is calculated as $-\log P$, where $P$ is the $P$ value of the test). A larger importance indicates a larger propensity for the levels of that bacterial specie or group to be differentially expressed in the caries-free versus the caries-active group. *S. parasanguinis* appears to be the most differentially expressed bacterial marker of caries, followed by *Abiotrophia defectiva*.

Figure 16

| Table 5: Drug Monitoring in Saliva, *from Kaufman 2002* ||
|---|---|
| Therapeutic Drugs | Drugs of Abuse/Recreational Drugs |
| Antipyrine | Amphetamines |
| Caffeine | Barbiturates |
| Carbamazepine | Benzodiazepines |
| Cisplatin | Cocaine |
| Diazepam | Ethanol |
| Digoxin | Marijuana |
| Ethosuximide | Nicotine |
| Irinotecan | Opioids |
| Lithium | Phencyclidine |
| Methadone | |
| Metoprolol | |
| Oxprenolol | |
| Paracetamol | |
| Phenytoin | |
| Primidone | |
| Procainamide | |
| Quinine | |
| Sulfanilamide | |
| Theophylline | |
| Tolbutamine | |

DIAGNOSTIC MOUTHPIECES

PRIOR RELATED APPLICATIONS

This case claims priority to 61/857,089, filed Jul. 22, 2013, and 61/870,534 filed Aug. 27, 2013, each expressly incorporated by reference in its entirety for all purposes.

FEDERALLY SPONSORED RESEARCH STATEMENT

Not applicable.

FIELD OF THE INVENTION

This invention relates to bite plates, originally intended for orthodontic remodeling uses, which are adapted to also provide diagnostic uses. Because orthodontic and dental care is far more frequent than medical care, such diagnostic mouthpieces provide unique opportunities for basic monitoring of health and early intervention.

BACKGROUND OF THE INVENTION

Orthodontics is the specialty of dentistry that is concerned with the study and treatment of malocclusion, which can be a result of tooth irregularity, disproportionate facial skeleton relationship, or both. Orthodontics treats malocclusion through the displacement of teeth via bony remodeling and control and modification of facial bone growth.

This process has been accomplished for hundreds (even thousands) of years using static mechanical forces to induce bone remodeling, thereby enabling teeth to slowly move through bone. In modern orthodontics, an archwire interfaces with brackets that are affixed to each tooth and the two components together are called braces. As the teeth and bones respond to the pressure applied via the archwire by shifting their positions, the wires are again tightened to apply additional pressure. This widely accepted approach to treating malocclusion takes about twenty-four months on average to complete, and cannot be rushed by applying more force because of the risk of root resorption.

In addition to static forces, it was recently proposed that cyclic forces could also be used for orthodontic remodeling. Kopher and Mao assessed cyclic forces of 5 N peak-magnitude at 1 Hz in rabbits, while Peptan and Mao assessed cyclic forces of 1 N at 8 Hz in rabbits, and Vij and Mao assessed cyclic forces of 300 mN at 4 Hz in rats. In aggregate, the data from these three studies indicated that cyclic forces between 1 Hz and 8 Hz, with forces ranging from 0.3 N to 5 N, increased the rate of bone remodeling. Rates depended on different methodologies, but increases of 2.5 times with vibrational forces were common.

The early Mao studies provided a basis for both possible efficacy and likely safety for using vibration in humans to assist orthodontic tooth movement, but the animal studies needed to be repeatable in humans, and the devices used by Mao and the others were completely unsuitable for human clinical work. Furthermore, the rabbit experiments were cranial suture growth and facial length experiments, not orthodontic, and the risk of root resorption is a complicating factor in translating Mao's work to orthodontics.

OrthoAccel® Technologies Inc. invented and tested the first commercially successful dental vibrating device, as described in US2008227046 and related cases, designed to apply cyclic forces to the dentition for accelerated remodeling purposes. Both intra-oral and extraoral embodiments are described in US2008227046. The bite plate is specially designed to contact occlusal as well as lingual and/or facial surfaces of the dentition, and thus is more effective than any prior art devices in conveying vibrational forces to the teeth, transmitting vibration in two axes. Finally, the device is slim, capable of hands free operation, lacks the bulky headgear of prior art devices, and has optimized force and frequency for orthodontic remodeling. Thus, its comfort level and compliance was also found to be high, with patients reporting that they were satisfied with the device, especially after the motor was redesigned to be quieter and smoother, as described in US2010055634 et seq. In fact, this device has been marketed as AcceleDent® and AcceleDent® Aura in the United States and several other countries and has achieved remarkable commercial success since its recent introduction. Further, the device was shown in clinical trials to speed orthodontic remodeling as much as 50%, and is truly a breakthrough in orthodontic technology (Kau 2010; see also clinicaltrials.gov). AcceleDent® represents the first successful clinical approach to accelerate orthodontic tooth movement by modulating bone biology in a non-invasive and non-pharmacological manner.

As the AcceleDent® device increases in popularity, it provides a unique opportunity for the orthodontist to monitor general health status and provide early intervention. Patients using traditional orthodontics, such as braces or aligners, are already using the AcceleDent® device daily for orthodontic remodeling for a period of a year or more. Thus, if the bite plate was combined with a simple and robust diagnostic platform, the orthodontist could provide primary health status information to his or her patients. Furthermore, since dental care is typically twice a year or yearly, whilst medical visits are far less frequent, a device that combined dental/orthodontic care with diagnostic information could provide an unprecedented ability to conveniently monitor patient health status and allow early intervention.

Several patents are already directed to salivary testing for various diseases, including various cancer, oral cancer, periodontal disease, stress, and the like. See e.g., US20100196941 (periodontal); US20120028261 (periodontal); US20100210023 (oral cancer); WO2007081306 (stress); US20080183101 (oral health). However, none of these applications contemplates combining such testing with a device that is already in daily use by patients.

Indeed, periodontal disease, gingivitis and caries are likely to be of particular interest to dental practitioners. Markers for periodontal disease activity include FAS, interleukin 1 beta (IL-1B), IL-6, IL-8, IL-12A, IL-17B, DEFB4, CTSS, CARD10, BGN, BE, LCN8, lactoperoxidase (LPO), aspartate aminotransferase (AST), alkaline phosphatase (ALP), aminopeptidases, beta glucuronidase, PGE-2, MMP-8, MMP-9, MMP-13, telopeptide, osteocalcin, and CRP. Indeed, at least three substances (peroxidase, hydroxyproline and calcium) are known to be significantly increased in the saliva of patients with periodontitis.

Thus, what is needed in the art is a simple robust diagnostic platform that is combinable with mouthpieces that are already in regular use by patients.

SUMMARY OF THE DISCLOSURE

This disclosure describes a diagnostic mouthpiece having diagnostic indicators thereon that can react with salivary biomarkers, providing e.g., a color change, and indicating the presence or absence of a marker or biomarker, or even indicating the approximate concentration of the marker or biomarker. Any salivary marker or biomarker can be used herein.

In preferred embodiment, the diagnostic indicator can be a dried antibody that is specific for a particular salivary biomarker, but the test can also be combined with other diagnostic indicators, such as pH reagents, substrates for salivary enzymes, ammonia indicators, as well as color indicators for e.g., nitric oxide (NO), zinc, phosphate, calcium, *Lactobacilli* and *Streptococcus mutans* and the like.

In some embodiments, the diagnostic indicators are contained on or in an absorbent pad that can be easily removed, and passed to the health care provider for more sophisticated testing. For example, cells can be eluted from the pad, lysed and PCR amplified for particular biomarkers. However, in most cases a simple binding and color change indicator would be preferred as amenable to home use. In practice, if the patient detects the color change, he or she informs the orthodontist or dental practitioner, so that further tests and/or interventional measures can be taken.

In yet other embodiments, the pad is sold separately from the mouthpiece, and thus can be used with a patient's existing mouthpiece. The pad can be peel and stick, but the adhesive may be optional if the pad is only to be used on an upper horizontal surface. Mouthpieces of many different types are already in wide use, e.g., as sport mouth-guards, bruxism mouth-guards, mandibular advancers, and the like. Peel-and-stick pads can also be sold for use with aligners and positioners.

The pad can be provided with an adhesive backing and stuck to any surface, but can be placed on the outer facing surfaces of the device, as opposed to teeth facing surface, as this will not interfere with the function of the device, and will provide the best access to saliva. However, placing a pad between the occlusal surfaces is also possible.

In other embodiments, where unidirectional travel of salivary fluid is desired, the pad can be contained inside the bite plate, with only one edge free to contact salivary fluid. In this configuration, the salivary fluid will wick by capillary action past the diagnostic indicators, allowing the use of well known dip-stick or "lateral flow" technology, such as is used in home pregnancy kits, to be employed. Alternatively, the pad can be covered with a flexible water proof coating, leaving at least one edge free for salivary ingress.

In another embodiment, the patient is sent such a diagnostic indicator pad monthly or at any appropriate time interval. The patient is instructed to apply the pad to the mouthpiece for the appropriate period of time and instructed to contact a particular number or website on the indication of a positive results. Alternatively, a patient can be sent home with e.g., a year's supply of diagnostic pads or diagnostic mouthpieces, and reminded by e.g., cell phone, text or email to repeat the test at an appropriate time interval. In yet another embodiment, testing occurs on biannual patient visits to the dental healthcare provider.

The following conditions are among those that can be detected through saliva testing: adrenal conditions (such as Cushing's disease/syndrome and Addison's disease), altered female hormone states (such as polycystic ovary syndrome [PCOS], menopause, anovulation, and hormonal alterations in cycling women), altered male hormone states (such as hypogonadism/andropause and hyperestrogenic states), metabolic disturbances (such as insulin resistance, diabetes, and metabolic syndrome), benign and metastatic neoplasms (such as breast cancer, pancreatic cancer, and oral cancer), infectious conditions (such as HIV, viral hepatitis, amoebiasis, and *helicobacter pylori* infection), and allergic conditions (such as food allergy). Testing for drugs of abuse, nicotine, or alcohol is also possible. Of course, oral infections, caries, gingivitis and periodontal disease can also be detected per the invention devices. More details are provided in the attached tables (FIG. 7-16), but these lists are not comprehensive.

Particularly preferred are diagnostic indicators for periodontal disease. For example, Interleukin-1β (IL-1β), interleukin-6 (IL-6), and matrix metalloproteinase-8 (MMP-8), calcium, peroxidase and zinc may be useful for diagnosing periodontal disease.

Any detection method can be used, including the use of fluorescent dyes, enzyme conjugated systems, and the like. However, direct, single step detection methods may be preferred as easily implemented in a home environment. Such methods are described, in e.g., U.S. Pat. No. 6,399,295, WO1998029746, US20130022961, US20120322086, US20130017559, US20130022969, U.S. Pat. No. 6,656,744, U.S. Pat. No. 8,377,643, U.S. Pat. No. 5,770,460, U.S. Pat. No. 8,377,710, U.S. Pat. No. 5,798,273, U.S. Pat. No. 7,605,004, U.S. Pat. No. 7,344,893, and the like.

Many diagnostic indicators are already commercially available by home test, and can easily be adapted for use herein. Machery-Nagel®, for example, makes several spot test strips that require only dipping in the sample for use and then reading the color change after a certain time interval. These tests include strips for zinc, ammonium, nitrite, nitrate, calcium, peroxide, and phosphate, and many others. The reagents of any of these spot test strips can be used as diagnostic indicators in the invention.

For example, calcium is believed to be negatively related to caries. The Gallade Chemical® strip test for calcium is based on the formation of a complex between calcium ions and glyoxal-bis-2-hydroxyanil in the presence of hydrogen peroxide. Another calcium spot test uses the Patton and Reeder's indicator (PR) as the indicator. This blue dye forms a complex with the calcium ions, changing color from blue to pink/red in the process. Failure to show a pink color would be indicative of caries. Zinc likewise has a negative correlation with caries, and can be detected in by reaction with e.g., dithizone to form a red complex.

High NO is usually indicative of caries, and may be part of the body's response to the infection. Indicator dyes for nitric oxide, nitrite and nitrate are also commercially available (e.g., from Invitrogen®) and include 4-amino-5-methylamino-2',7'-difluorofluorescein (DAF-FM), 2,3-diaminonaphthalene (DAN), 1,2-diaminoanthraquinone, N-methyl-4-hydrazino-7-nitrobenzofurazan (for nitrite $-NO_2^-$). Spot indicator dyes for pH also exist (see FIG. 10).

Amylase and many other enzymes can also be tested in spot based tests using enzymatically driven color changes. For example, the Rapignost-Amylase (Behring®) test strip for the rapid determination of alpha-amylase in urine or saliva and the amylase-reaction is recognized as a reddish-violet coloration of the reaction zone. The Phadebas Amylase Test (PAT), originally developed by Pharmacia®, is based on DSM-P, microspheres in which a blue dye has been chemically bound. Alpha-amylase degrades the microspheres, thereby releasing the blue dye.

The benzoyl-DL-arginine-b-naphthylamide (BANA) test is a chair-side test that can detect the presence of one or more anaerobic bacteria commonly associated with periodontal disease, namely, *T. denticola, P. gingivalis*, and *T. forsythensis*. It is used together with a chromogenic diazo reagent that, after BANA hydrolysis, reacts with b-naphthylamide, producing a permanent blue color (positive test). Although not yet developed as a strip test, it is expected that the reagents can be applied to a solid phase testing pads, such as described herein.

Peroxidase test strips are also already available, e.g., from Merck® and Millipore®, and can be adapted for use in the invention. There are several chromogenic substrates that can be used to test for the presence of peroxidase including o-tolidine hydrochloride, Amplex Red Reagent from Invitrogen®, 2,2'-azino-bis(3-ethylbenzthiazoline-6 sulfonic acid) diammonium salt (ABTS); 2,2'-Azino-bis(3-ethylbenzthiazoline-6-sulfonic acid), and the like.

Additionally, several immunogenic salivary biomarker tests are already commercially available. For example, Salimetrics® offers a multistep melatonin immunoassay, alpha amylase, cortisol and many others (shown in Table 1). Any of these immunoassays can be converted into a lateral flow format as described herein.

In other embodiments, for example, where the tests are performed by an orthodontist or other dental practitioner in an office setting, the diagnostic indicator pad can be removed and assessed in an instrument, such as fluorescence detector and the like.

In one lateral flow embodiment, a U-shaped absorbent pad is provided with several diagnostic indicator assays arranged perpendicularly to the inner edge, so that saliva contacting the inner edge will diffuse past the indicator and any secondary components, producing a color change on the outer edge of the U-shaped pad. This embodiment requires a dedicated mouthpiece design, which houses the pad inside the U-shaped mouthpiece, leaving the inner edge at least partially open for saliva contact. Snap fit posts can provide support for the inner edge of the mouthpiece if needed, but if correctly sized, the pad may provide sufficient support instead. A dummy pad can be provided if the device is intended for continual use, but alternatively, single use mouthpieces can be provided instead.

The dedicated mouthpiece is not needed, however, if the pad itself is covered with a transparent coating leaving a single open edge. For example, plastic sheets or other waterproof flexible material can be placed over a lingual shaped pad, heat sealed at the edges, and if adhesive is needed for good pad/plastic contact, the adhesive can be laid between the lateral flow assay regions. Then, the inner portion of the pad can be punched out, leaving a U-shaped indicator pad with a single open edge for lateral flow. An adhesive backing and protective covering can also be added to one side of the pad, making a convenient peel-and-stick diagnostic pad that can be added, e.g., to the AcceleDent® bite plate or any other mouthpiece.

While similar in concept to the existing dip-stick tests that are housed inside a plastic case, these covered diagnostic mouthpiece pads differ in important ways. First of all, the plastic coating is quite flexible, allowing the user to mold the entirety of the diagnostic pad to the teeth or mouthpiece. Rather than being supportive, the plastic coating is only intended to prevent fluid entry except at the open portion. In the commercial dip-sticks, the casing is quite stiff, usually opaque and has a window through which the color can be read. This housing is intended to be supportive, providing a convenient stiff tool that the user can handle in applying sample to the test strip contained inside.

If desired, linear peel-and-stick strips, rather than U-shaped strips can be made for use with aligners, which have a small footprint. However, the U-shaped can also be used with aligners, since all dentition provides U-shaped occlusal surfaces. When a linear strip is used, it may not have enough width for a lateral test to be run perpendicularly to the length. However, two lateral flow tests can still fit on a single strip using the short ends of the strips as the open edge, and spot tests can be arranged sequentially, requiring little space, and the long edge left open for salivary ingress.

In preferred embodiments, the mouthpiece has a connector protruding from a midline thereof that connects to an extra-oral orthodontic remodeling device. In other preferred embodiments, the mouthpiece is shaped to fit into the existing AcceleDent® models, and thus the connector has a particular size and shape, as detailed herein.

In yet other embodiments, the bite plate omits the connector and has fitted therein one or more e.g., coin vibrators or other tiny vibratory source(s), which are operably coupled to one or more coin battery(s) or charged capacitor(s), which are operably coupled to an optional processor for controlling the device and monitoring usage compliance. Thus, the entire device is intra-oral. Intra-oral mouthpieces are preferably used with separate diagnostic pads, unless the price point is so low as to allow a single use device.

In yet other embodiments, the device or driver uses other treatment modalities in place of or in addition to pulsed or cyclic forces (aka vibration). Thus, the device can be fitted with IR light source, EM field source, microelectronic pulse source, and the like. However, in preferred modalities, the device includes a vibrational source, since vibration has already been proven in clinical trials to provide 50% faster orthodontic remodeling.

In the vibrating drive embodiment, a patient wearing additional fixed appliances, such as braces, aligners, tads, palatial expanders, and the like, bites on the bite plate to hold it firmly during use. No headgear is needed, and the orthodontic forces are provided by the fixed appliances. The absorbent pad, which can be on the upper surface, upper and lower, or all surfaces of the bite plate, or can be inside the bite plate, with only one edge accessible (if lateral flow is needed). Vibration is applied for about 20 minutes, and during this time, saliva will permeate the pad, allowing a antibody antigen reaction, enzymatic reaction or simple binding reaction to take place, which can then be detected, e.g., by color change, as is well known in the art.

The bite plate designs of the AcceleDent® device (see e.g., US2008227046, US2010055634) consists of a U-shaped bite plate that contacted the occlusal surfaces of the dentition. Also included is a vertical edge on the facial side of the U-shaped plate, and a partial vertical edge on the lingual side. The occlusal contact and facial/lingual contact allow the vibration to be in a gingival-apical (up-and-down) direction, as well as mesial-distal (front-to-back) direction. The vertical edges and horizontal base, thus allows the vibration to be transferred to the teeth in two axes, and are much preferred over a simple flat bite plate. The lingual edge also serves to keep the bite plate correctly positioned over the teeth.

In some embodiments, the bite plate has an inner core that is made of e.g., metal, ceramic or a rigid plastic, such as acrylate or polycarbonate. The inner core is sufficiently stiff so as to transmit vibration to the mouthpiece and thence to the teeth. The inner core can be flat (except for the connector), or can be shaped to have the vertical edges, as desired.

The inner core is connected to or is integral with a connector at the median line, and projecting extra-orally, which serves to operably connect the bite plate to an extraoral driver. The connector can be of any suitable shape, but preferably provides a snap fit to the extraoral driver. The connector is preferably integral with the core, but can be a separate component attached thereto, or can have separate components added to an integral connector, e.g., a spring.

The inner core is covered with a polymeric coating or cover, wherein the outer surface thereof is shaped to contact all occlusal surfaces and at least facial incisor surfaces, surfaces, and possibly more. Where no inner core is included in the dental plate, the entirety of the bite plate is molded to have the desired shape, including the vertical edges or rims.

The bite plate is combined with any treatment modality, including vibration, laser light, IR light, electromagnetic pulses, electrical micropulses, heat, and the like, but one preferred embodiment is the extraoral vibrator described in US2008227046 and US2010055634. The bite plate is preferably used with the existing extraoral vibrational device, which is already cleared for marketing in the US and several other places and already has proven efficacy. Thus, the biomarker bite plate ideally has the same connector, and can be used with the existing driver.

In addition, the same principles can be applied to a completely intra-oral device, wherein the vibratory source or other treatment modality, power source and wiring are mounted directly on the bite plate.

Preferred extraoral vibratory sources are described in the OrthoAccel patents cited herein, and in particular include a device that vibrates at 1-400 Hz and 0.05-% newtons. Preferred is a single frequency between 20-40 Hz, and at a single force between 0.1-1 Newtons (1 N=1 kg m/s$^2$). More preferred, the device vibrates at a single frequency between 20-40 Hz with a variation of less than 2 Hz, and at a single force between 0.1-0.5 Newtons with a variation of less than 0.05 Newtons. Even more preferred the device vibrates at 30 Hz with a variation of less than 2 Hz, and at 0.2 or 0.25 Newtons with a variation of less than 0.03 Newtons. Variation should be measured under conditions of use, e.g., by a patient or simulated patient use for 10-20 minutes.

A double blind clinical trial (see clinicaltrials.gov) has shown that in daily use (67% compliance), the device will speed remodeling by 50% (e.g., one year instead of the typical two).

By "U-shaped" what is meant herein is that the shape follows the curvature of the dentition, e.g., the biting surfaces of the teeth are in a substantially U-shaped curvature.

When we refer to contacting "the teeth" or "the dentition" or similar phrase herein, what is meant is the teeth of both arches, unless the maxillary teeth or mandibular teeth are specifically referred to, or teeth are named separately. Nevertheless, the bite plate need not contact every single tooth, since by definition malocclusions may result in one or more teeth being considerably out of alignment and/or occlusion.

By "treatment modality" what is meant is a mode of action that causes an orthodontic benefit.

By "treatment modality source," what is meant is a device or component of a device that provides the treatment modality. For example, vibration is an orthodontic treatment modality and a vibratory source provides vibration. A vibratory source could also be called a vibrator. Another treatment modality is infrared or ultraviolet light, and an LED could be an exemplary light source.

An "extraoral driver" is the extraoral component that provides the treatment modality, and in preferred embodiments, is a housing enclosing a treatment modality source such as a vibrator or laser, a processor, a battery or other power source, and the wiring needed to operatively couple or operate same, and wherein the housing has a socket for receiving the connector of the bite plate (or vice versa). The housing would preferably be at least water resistant or even waterproof. Preferably, the housing also contains a processor to control the treatment modality source, and preferably it also records and transmits usage compliance data.

By "recording and transmitting" data what is meant is that the device records or captures data, such as date, time and duration of each use, and can then transmit that data to a user or other device, such as a smartphone, stand alone PC or the internet. USB ports, wireless data ports such as the Bluetooth, and the like, can provide this functionality. Research has shown that the ability to monitor usage increases compliance, especially in younger and teen patients.

By "usage compliance data," what is meant is data relating to how often and how long a user actually employs the device. Thus, usage compliance data can include the date, time, length of use, and the like.

By "rigid," herein in reference to the inner core, what is meant is that the core is stiff enough to transfer at least 0.1-0.5 N, preferably 0.02 or 0.025 N of vibration to the teeth.

By "daily" what is meant is at least 67% compliance in daily use. Although perfect compliance would obviously be preferred, significantly increased speed of orthodontic remodeling was seen at only 67% compliance in the Kau study.

By "diagnostic indicator," what is meant is that one or more reagents are present that allow the testing of a salivary marker for disease, or a biomarker for disease.

By "diagnostic" what is meant are methods of detecting disease, both early and late stage, but preferably very early stage, as well as predicting future disease and/or determining predisposition to disease.

By a "dental disease" what is meant herein is gingivitis, periodontal disease, caries, and the like.

By "biomarker" what is meant is a protein and or its genetic coding sequence that is indicative of either disease or predisposition for disease. A "marker," in contrast, includes simple chemicals such as calcium, phosphate and zinc.

By "diagnostic pad," what is meant is a solid substrate that is porous or absorbent, at least in part, so as to allow capillary flow or wicking of saliva.

By "lateral flow test strip," what is meant is a diagnostic pad having reagents sequentially placed so that capillary flow of the saliva allows a reaction to occur, e.g., a sandwich immunoassay.

By "test strip" or "spot test strip" what is meant is a diagnostic pad that can simply be dipped in sample, or otherwise contacted with sample, and provide a color change at one or more spots on the strip. No lateral flow is required, because such tests are direct color change assays.

By "removable protective layer," what is meant is a flexible layer that can be peeled away from the adhesive backing, so that the diagnostic pad can be applied to a mouthpiece. A wax or polymer coated paper is often used for this, but foil or plastic can also be used.

By "waterproof," herein what is meant is that the coating does not allow the ingress of saliva over the period of a single use, e.g., 10-60 minutes. The coating need not be waterproof for extensive periods of time however.

By "flexible," with respect to the coating material, what is meant is that the coating has enough flex to be comfortable gripped by the teeth, or enough flex to mold to the mouthpiece of choice. Usually, a thin plastic layer or a polymer-coated paper will be used for the flexible waterproof coating.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated. When used in the context of part dimensions, the term includes those tolerances that are acceptable and still allow the parts to operably connect. Where a part material is flexible, the tolerance may be slightly higher, but a rigid part made of metal will typically have smaller tolerances.

The use of the term "or" in the claims is used to mean "and/or" unless explicitly indicated to refer to alternatives only or if the alternatives are mutually exclusive.

The terms "comprise", "have", and "include" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Thus, the term "consisting essentially of" does not exclude immaterial elements, such as packaging, instructions for use, and the like, but does exclude headgear, toothbrush bristles and the like, which materially change the nature of the invention.

BRIEF DESCRIPTION OF THE DRAWINGS

FIGS. 6A-E show an exemplary AcceleDent® mouthpiece A, the inner core B and connector details C-E.

FIG. 7 salivary test kits, available from Salimetrics®.

FIG. 8 salivary biomarkers, from Soo (2007).

FIGS. 9A-C display various salivary markers, from Rathnayake (2013).

FIG. 10 displays various pH indicator dyes that can be used with the invention.

FIG. 12. Various markers known to be associated with oral disease, from Pederson (2005).

FIG. 13. Importance of bacteria probes according to their individual discriminative power. Bacterial species or group are indicated along the y-axis. Shaded bars indicate the importance of the species as measured by the Wilcoxon rank-sum score (the score is calculated as −log P, where P is the P value of the test). A larger importance indicates a larger propensity for the levels of that bacterial species or group to be differentially expressed in the caries-free versus the caries-active group. *S. parasanguinis* appears to be the most differentially expressed bacterial marker of caries, followed by *Abiotrophia defective*, from Hart (2011).

FIG. 16 displays drugs of abuse and therapeutic drugs that are monitored in saliva, from Kaufman 2002.

DETAILED DESCRIPTION OF THE DISCLOSURE

Figure 1A:
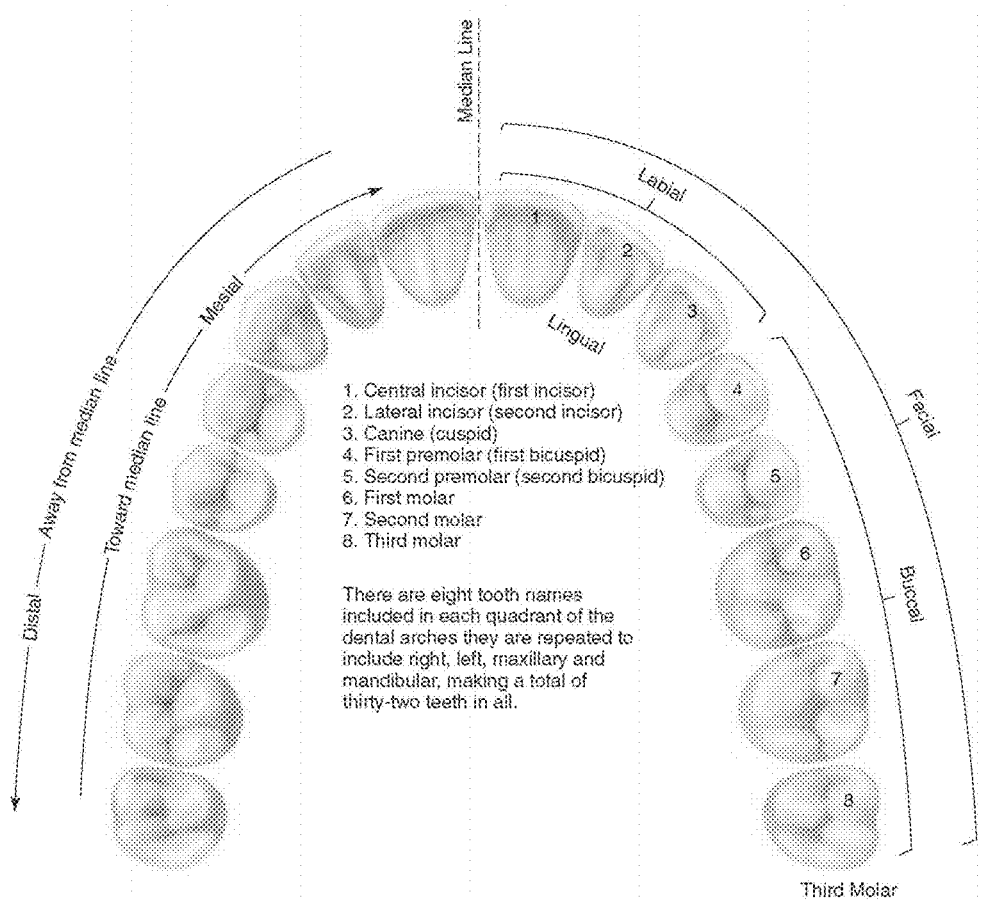
FIGS. 1A-B show standard dental nomenclature, which is employed herein. The central and lateral incisors and the cuspids are also known as "anterior" teeth, while the pre-molars and molars are "posterior."

The invention can comprise one or more of the following embodiments, in any combination:

---

A diagnostic mouthpiece for oral use, said mouthpiece comprising:
a U-shaped bite plate to contact occlusal surfaces of a patient's teeth;
said U-shaped bite plate comprising an absorbent material that is:
a) on one or more surfaces thereof, or
b) between two surfaces thereof with at least one edge accessible for saliva ingress; said absorbent material comprising diagnostic indicators specific for at least one salivary marker or salivary bio marker.
The U-shaped bite plate comprising vertical edges to contact the facial surfaces of said patient's teeth.
The U-shaped bite plate comprising vertical edges to contact both facial and lingual surfaces of a patient's teeth.
The U-shaped bite plate having a connector protruding from a midline thereof, said connector for reversible coupling to an extra-oral orthodontic remodeling device.
The extra-oral orthodontic remodeling device includes a water resistant housing containing a vibrator operably coupled to a power source operably coupled to a processor for controlling device usage.
The processor also records and transmits compliance data.
The vibrator vibrates at a selected frequency from 20 to 40 Hz and at a selected force from 0.1 to 0.5 Newtons.
The vibrator vibrates at 30 Hz and 0.2 Newtons.
The connector is a cylindrical post having a base end near said bite plate, said cylindrical post being 5.5 mm diameter and about 10.25 mm in length and having a groove circumnavigating said cylindrical post at 4 mm from said base end.
A diagnostic pad for oral use, said diagnostic pad comprising an absorbent material in a U-shape for contacting occlusal surfaces of dentition, said absorbent material comprising at least two diagnostic indicators thereon, for testing at least two salivary markers or biomarkers.
The diagnostic pad comprising a transparent flexible waterproof coating on three sides thereof, leaving one edge open for saliva ingress, and comprising at least one lateral flow immunological test.
The diagnostic pad comprising a transparent flexible waterproof coating on three sides thereof, leaving one edge open for saliva ingress, and comprising at least 4 lateral flow immunological tests.
The diagnostic pad comprising an adhesive backing on an outer bottom surface of said waterproof coating, said adhesive backing covered with a removable protective layer.
A diagnostic pad for oral use, said diagnostic pad comprising:
an absorbent material in a rectangular strip having two ends;

said absorbent material comprising at least two diagnostic indicators thereon for testing at least two salivary markers or biomarkers;
said absorbent material comprising a transparent flexible waterproof coating, leaving at least one open surface for saliva ingress;
said waterproof coating having an adhesive backing on an outer surface thereof, said adhesive backing covered with a removable protective layer. The diagnostic pad having two open edges at each of said two ends, and having a lateral flow immunological test at each of said two ends.

Figure 1B:
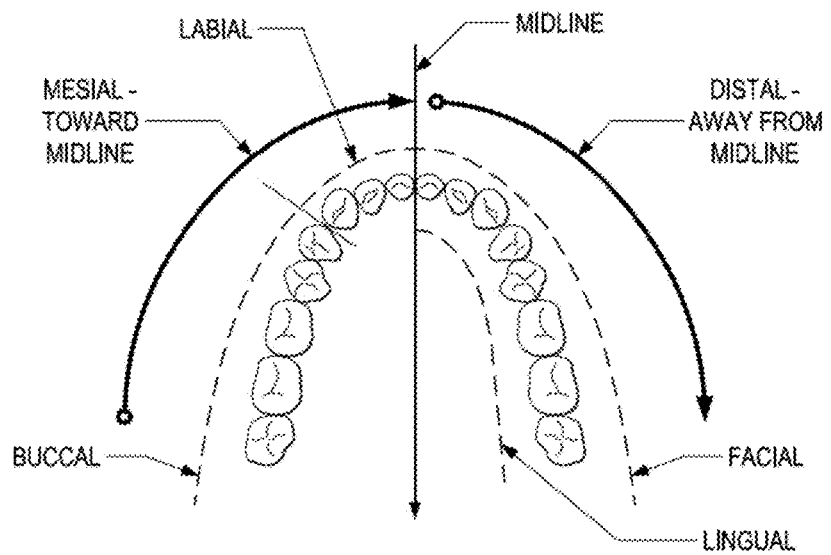

FIGS. 1A-B provides some general dental terminology, and is for reference use only. Standard dental and orthodontic nomenclature is used herein.

Lateral Flow Test Strips

Figure 2:
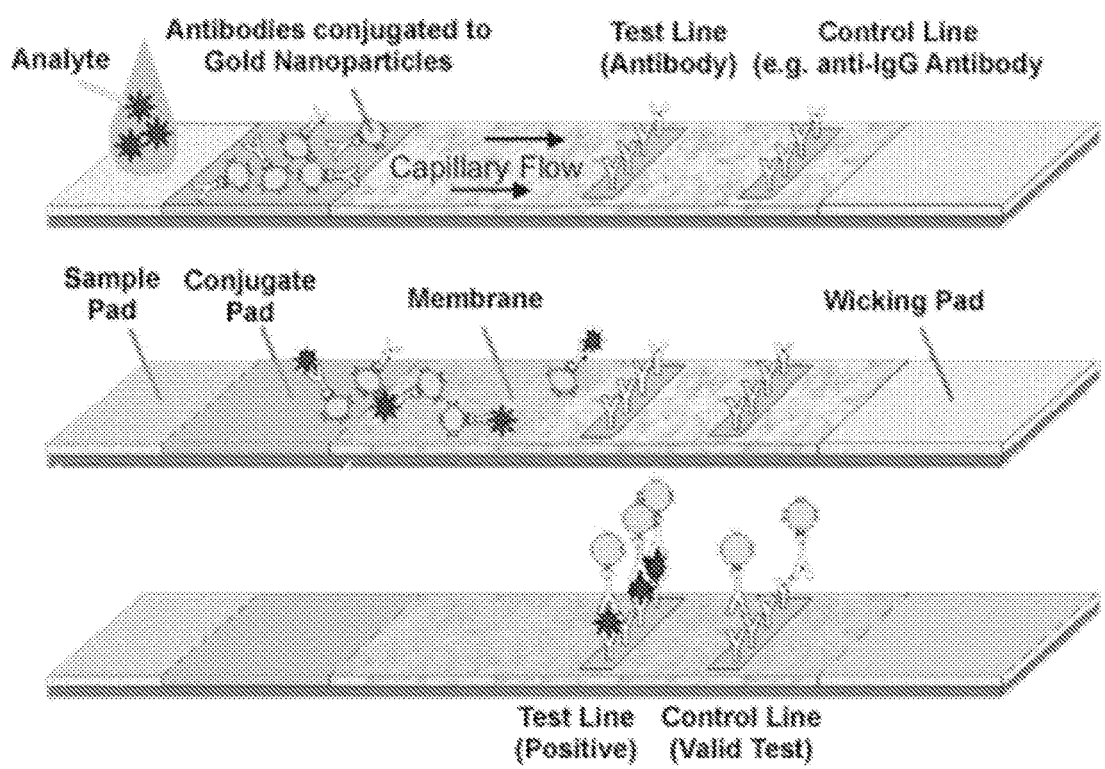
FIG. 2 shows a prior art lateral flow test strip. This design can be adapted for use in the invention, as shown in FIG. 4A-B.

FIG. 2 shows a common design for a lateral flow test strip for a sandwich immunoassay, comprising a sample pad, a conjugate pad with detection conjugate, in this case gold-based conjugate, test and control lines, often on a membrane, such as nitrocellulose, followed by another absorbent pad for wicking.

The sample pad is made of cellulose, glass fiber or other material where the fluid sample is applied to the lateral flow device and, if necessary, modifies it to improve the results of the assay. This might be by modifying pH, filtering out solid components, separating whole blood constituents, adsorbing out unwanted antibodies or some other test specific variable.

The conjugate pad is made of a non-absorbent material such as fiberglass pad, polyester, rayon or a similar material. The conjugate pad is of a synthetic material (at least when using a gold conjugate) to ensure the efficient release of its contents.

The detection conjugate, often a labeled antibody, is dried down and stays in place until a liquid test sample is applied to the sample pad. The liquid from the sample, by capillary action moves into the conjugate pad, re-hydrates the detection conjugate and allows the mixing of the sample with the conjugate. The complex of detection conjugate and analyte then moves into and up the membrane.

The signal reagents used in lateral flow tests have become much more varied as the technology advances. Tests may use colloidal metals such as gold or silver, carbon, a visible or florescent dye, magnetic particles, enzymes, latex beads impregnated with visual or fluorescent dyes, or a combination of these which are conjugated to either an antibody or antigen to generate signal. In early versions of lateral flow tests, latex was a common conjugate, however colloidal gold is probably the most commonly used signal reagent in use today. The reagent used as a signal reagent will affect whether a strip can be simply read visually or if it will require an instrumented reader.

The vast majority of the available assays contain gold, colored latex or another visually observable particle adsorbed with antibodies or antigens specific to the analyte being detected. If the strip will be read visually, the detection particle must be large enough to be seen but not so large as to overwhelm the antibody (or antigen) conjugated to its surface through steric hindrance. These particles usually run from 10-100 nm in diameter, but there can be exceptions.

Conjugate is added to the pad usually by immersion or spraying. In immersion, the conjugate pad is submerged in the conjugate-protein suspension. In spraying, the pad is coated using quantitative, directional aerosol dispenser, which is somewhat similar to an inkjet printer. Spraying offers much more control of the conjugate application and prevents dilution and washing away of the pad pretreatment, but it also adds a significant capital expense and can increase the complexity of strip manufacturing.

The nitrocellulose (NC) membrane consists of a very thin Mylar sheet coated with a layer of NC. The benefits of NC as an assay matrix are the reason why it so completely dominates the rapid test market. These benefits include low cost, capillary flow, high binding affinity for protein, ease of handling and cutting, as well as the ability of manufactures to varying thickness and components of the membrane to suit customer and market needs.

As with many immunological based assays, blocking may be necessary to prevent nonspecific binding of sample and conjugate to the test lines and to limit background along the membrane. This is especially true with NC membranes. Blocking is also used to control flow rates and stabilize test and control-line proteins. The blocking process involves immersion of the striped membrane in an aqueous solution of proteins, surfactants, and/or polymers. The membrane is then removed, blotted, and dried.

The detection conjugate/analyte complex then moves onto the membrane strip and migrates towards the capture binding protein, where it becomes immobilized and produces a distinct signal in the form of a sharp red line. A second line, a control, may also be formed on the membrane by excess detection conjugate, indicating the test is complete.

The standard for lateral flow tests is one test line and one control line placed on the NC membrane. These are usually closer to the absorbent wicking pad than to the sample/conjugate pads. Lateral flow assays may have more than one test line, but each additional test line can increase cost.

The absorbent pad, also called a wick or wicking pad, pulls fluid off of the membrane to allow the capillary flow of the membrane to keep flowing in the proper direction and at the proper rate. If an absorbent pad isn't used (or if it separates from the membrane so it is functionally absent), the sample and buffer will back flow down the membrane and could raise the background or possibly cause false positives. This can also occur if the absorbent pad selected for the volumes of buffer and sample involved is inadequate. Most absorbent pads are made from non-woven, cellulose fiber sheets. These pads can be manufactured in a variety of thicknesses and densities to suit the needs of the assay.

Due to the delicate nature of the materials used in a lateral flow immunoassay as well as the need to maintain a precise, direct contact between components to ensure proper reagent and sample flow, a backing card of some sort is usually needed, although in this instance the bite plate can provide the needed support. Usually, these are pre-treated with a pressure-sensitive adhesive selected for its stability in the assay and to insure it doesn't leach chemicals that may interfere with results. A related concern is that the adhesive is strong enough to properly bind the materials to the card but that it also doesn't flow too far into them and inhibit the capillary action by reducing the available bed volume. The adhesive card is initially covered with a liner, which may be pre-slit for easier assembly of test components. The backing card can be modified for use in this invention to cover additional surfaces, and the same manufacturing issues apply, although adhesive can be limited to areas between tests.

Many materials are available depending on the needs of the assay platform and manufacture configurations of the diagnostic tests. The more common materials are: polystyrene, vinyl, polyester (clear or opaque), and Mylar.

U-Shaped Diagnostic Pads

As can be seen, in many embodiments, the bite plate is generally U-shaped, following the curve of the dentition.

Preferably, the device is manufactured and sold in a Euro arch form, thus fitting the majority of North American and European patients, but a wider arch can also be made, so as to fit a majority of Asian patients, or the even wider Damon arch can be used.

Figure 3A:
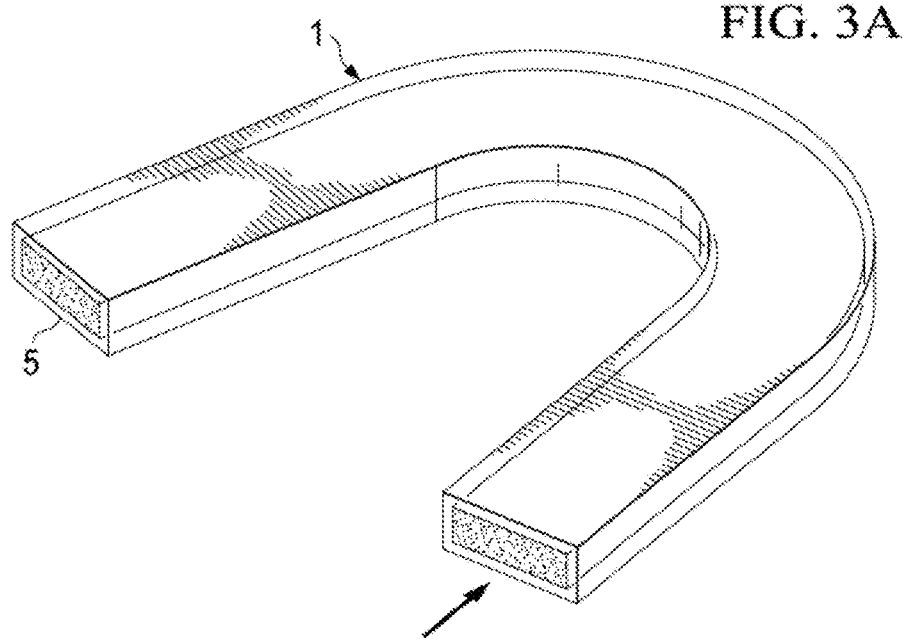
FIG. 3 shows a U-shaped diagnostic pad having a water-proof outer coating, wherein the end edges are open in 3A for saliva ingress, but the inner edge is open in 3B.
Figure 4A:
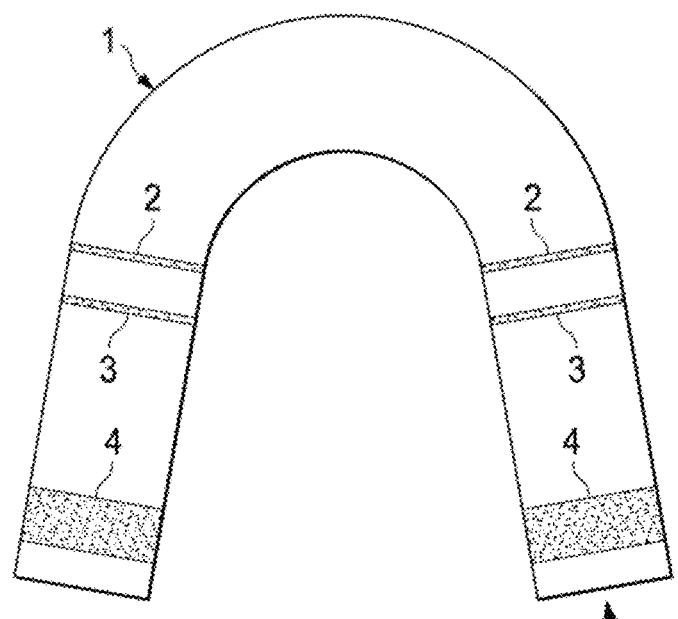
FIGS. 4A-B show top views of two diagnostic indicator pads that can be used with various mouthpieces, wherein the placement pattern of diagnostic indicators is varied.

FIGS. 3A and B and FIGS. 4A and B show the waterproof coating 5 and diagnostic pad 7 of device 1. In 3A, the ends are open (e.g., not covered with a waterproof coating), so that saliva enters pad 7 via these open edges (see arrow), whereas the remaining surfaces are covered with coating 5. In FIG. 4A, a top view of the diagnostic pad is shown, wherein saliva ingress via the ends. At least two lateral flow tests (see antibody lines 2, 3, 4 as described in FIG. 2) can be fitted on this device 1, and it is possible that two tests can be fitted at each end, providing a 4-immunoassay device 1. Alternatively, one or more of the tests can be a spot test.

Figure 3B:
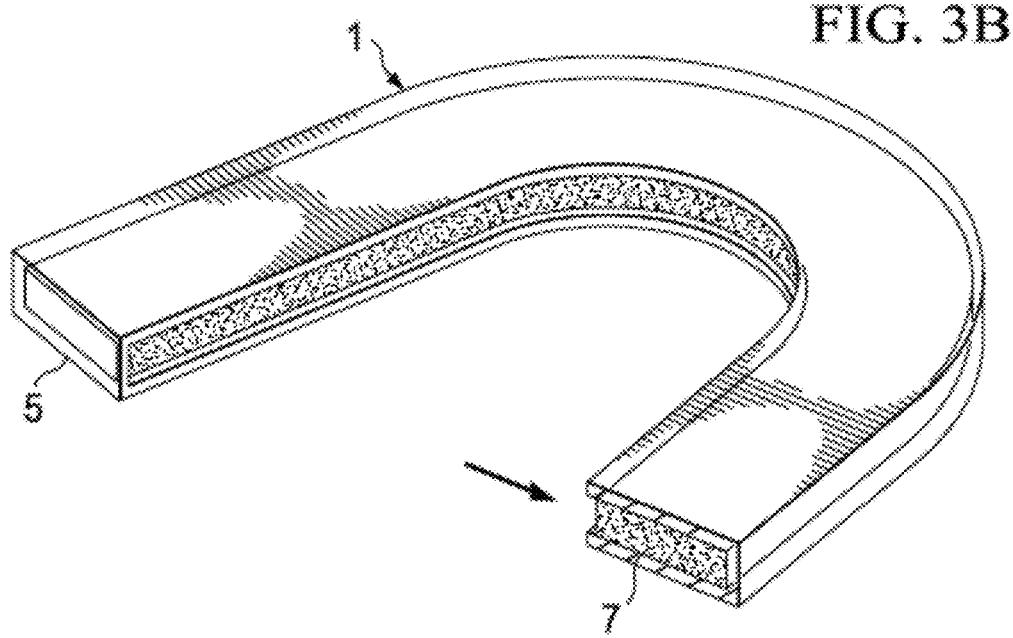
Figure 4B:
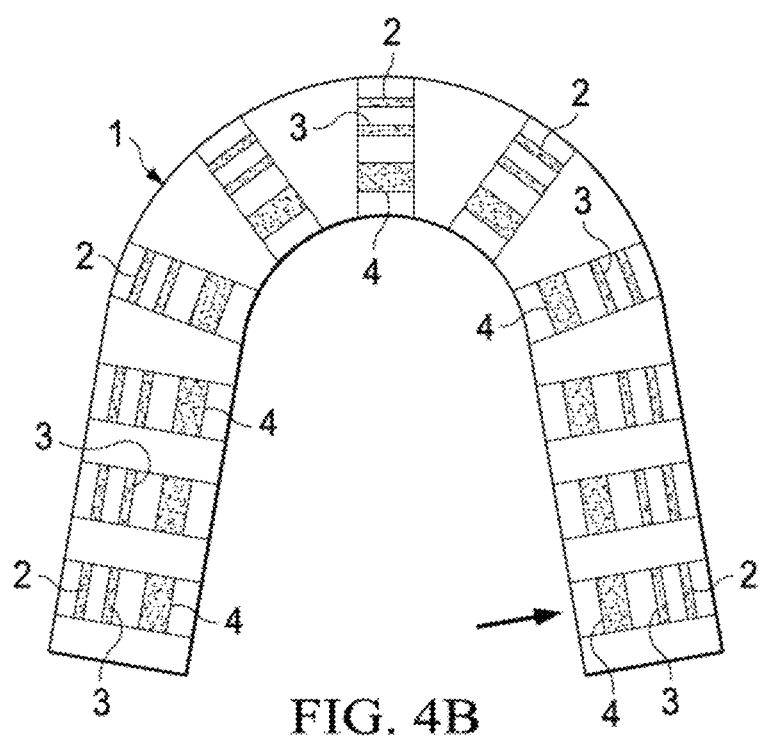

FIG. 3B shows another embodiment of the bite plate 1 with a transparent outer coating 5 over diagnostic pad 7, wherein one of the ends of the bite plate is cut across to show a portion in cross section. In 3B the coating is open on the inner edge of the bite plate so that saliva can ingress at this edge (see arrow) into the pad 7. FIG. 4B shows a top view of such a bite plate 1. In this embodiment, many lateral flow (2, 3, 4) and spot tests are possible.

Figure 5A:
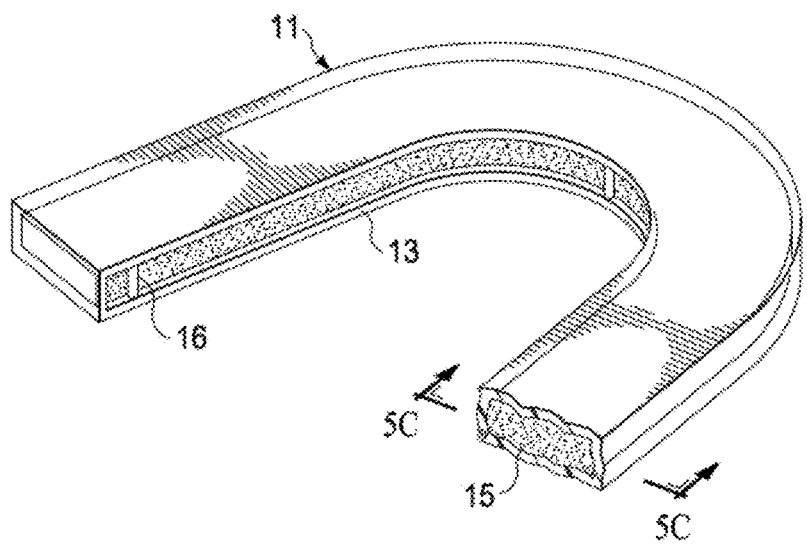
FIG. 5A shows a perspective view of a mouthpiece with open inner edge, into which a diagnostic indicator pad can be fitted. Although an inner core is not shown in this simple version, a mouthpiece with inner core and connector can be made in a similar way.
Figure 5B:
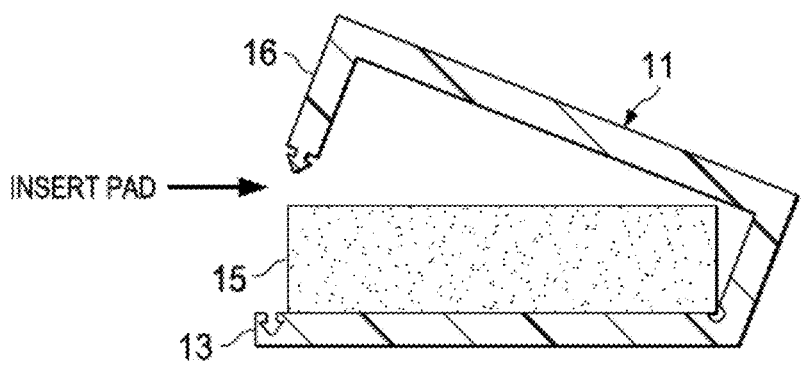
FIG. 5B shows a cross section of the mouthpiece of FIG. 5A, wherein the upper layer of the mouthpiece is spread apart from the lower layer, such that a diagnostic indicator pad can be inserted thereinto.
Figure 5C:
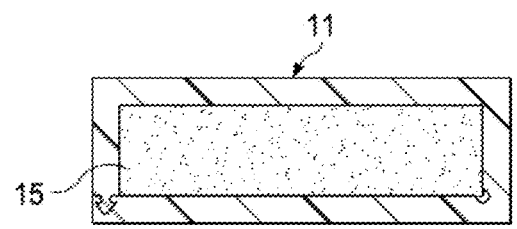
FIG. 5C shows the same cross section, wherein the mouthpiece is closed via some closing mechanism, herein shown a snap fitting connector.
Figure 11:
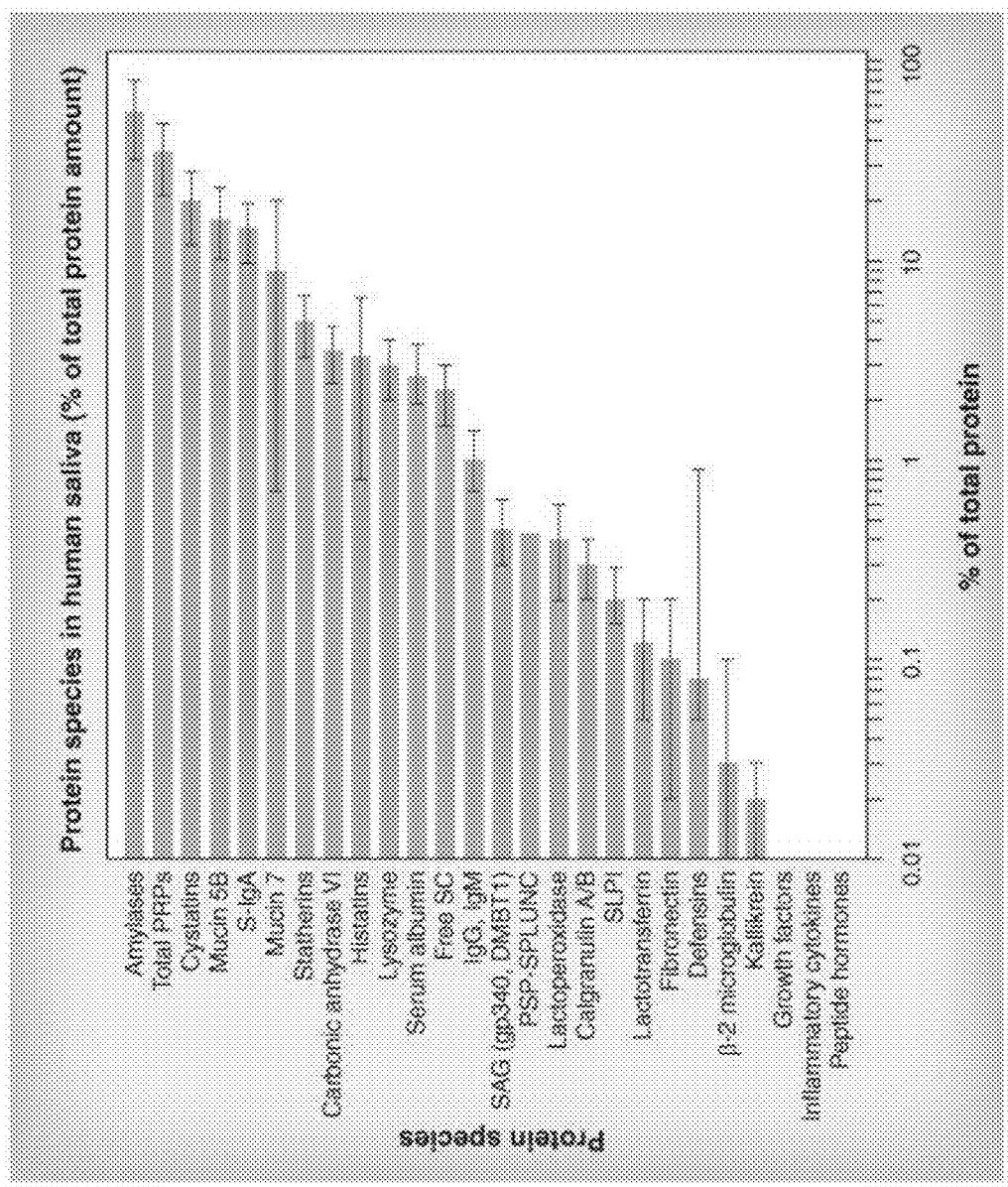
FIG. 11 salivary biomarkers and known ranges as a percentage of total protein, from Ruhl (2012).
Figure 14:
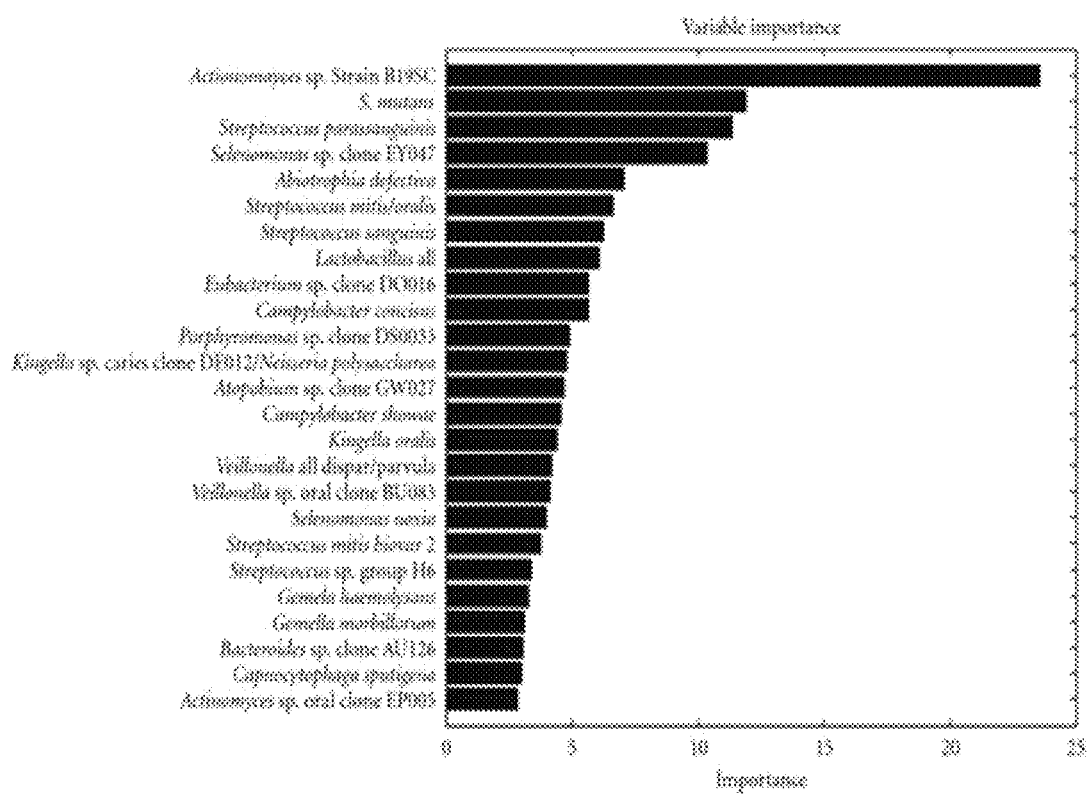
FIG. 14. Relative importance of bacterial DNA probes for classifying caries-active and caries-free samples using the random forest model. The 25 most significant DNA probes are listed, and the shaded bars display their importance. The five most important probes are *Actinomyces* strain B19SC, *Streptococcus mutans, Streptococcus parasanguinis, Selenomonas* sp. Clone EY047, and *Abiotrophia defective*, from Hart (2011).
Figure 15:
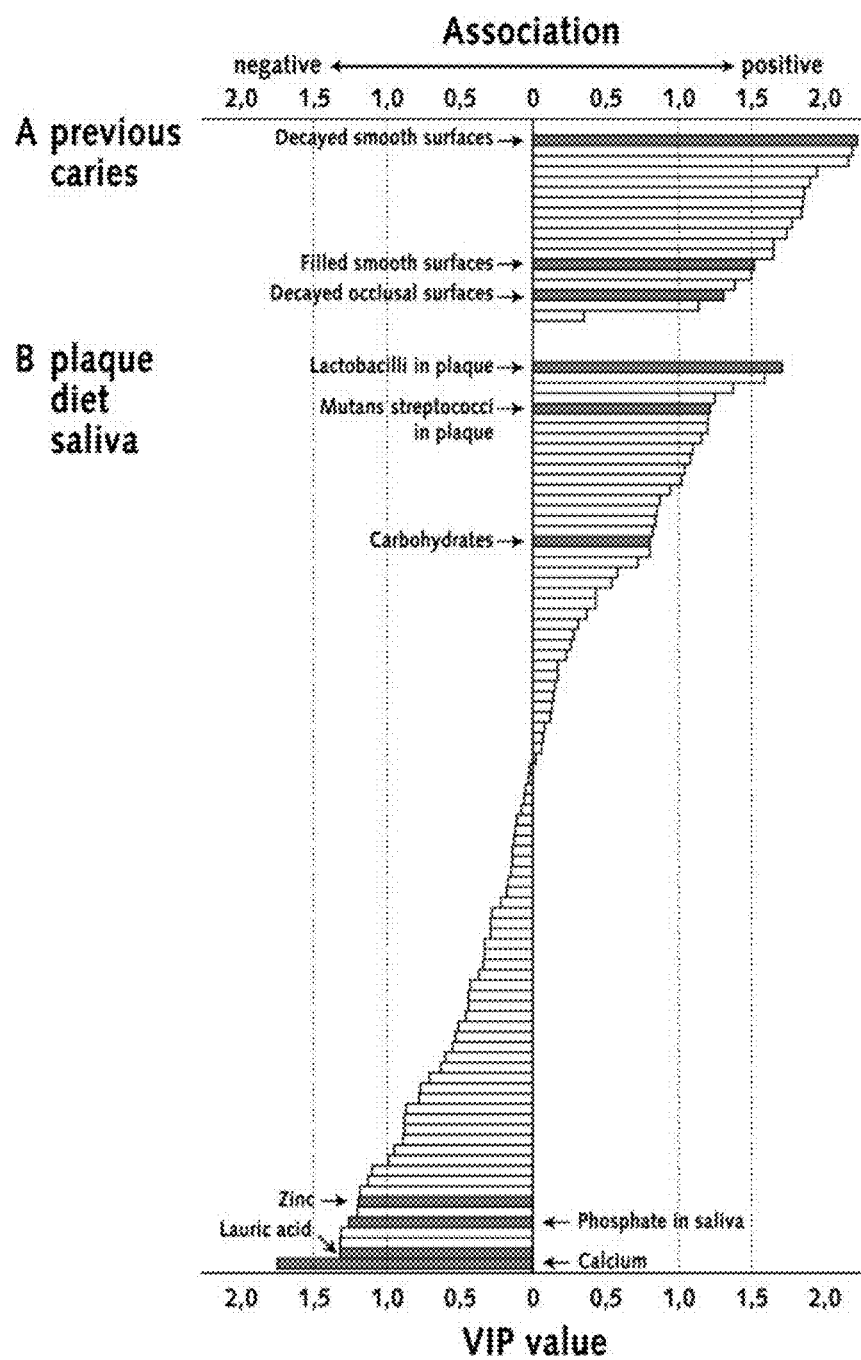
FIG. 15. Wide but shallow gliding scale of variables related to caries. Schematic picture illustrating the ability of the PLS method to give the relative rank of associations for multiple variables. Displayed is the gliding scale of all plaque, saliva and diet (n=88) and previous caries (n=18) variables in the case of incidence (model M4); from the most influential (VIP>1.0) positively associated variables (top) to the most influential negatively associated variables (bottom). Some variables are marked by arrows and bold bars, from Nordlund (2009).

FIG. 5A-C shows another variation, wherein the bite plate 11 can be opened and a new diagnostic pad 15 inserted thereinto. In FIG. 5A, 11 is the U-shaped mouthpiece, here shown as a simple flat U only, but can and probably would be more complex. Pad 15 is seen inside the bite plate, wherein one of the ends has been cut off to provide a cross sectional view, showing details of a post 16. The inner edge 13 is open, allowing for saliva ingress and closable posts 16 are shown.

FIG. 5B shows a more detailed cross section, wherein post 16 is shown in an open position, bite plate 11 being of sufficiently flexible material to allow lifting of the inner edge 13 and insertion of pad 15. In FIG. 5C, the posts are snap fit closed into a small opening shaped for same in the receiving surface, but other attachment or closure means are possible.

Commercial Bite Plates

FIG. 6A-E shows an exemplary bite plate for AcceleDent®, which can be modified to include the diagnostic pad of the invention. In more detail, FIG. 6A shows a bite plate 1000, having generally U-shaped base 1001 that contacts occlusal surfaces of the teeth, the base having front and back edges, one or both edges having a rim to contact the facial and lingual surfaces of teeth and/or gums. Thus, upper lingual rim 1002, lower lingual rim 1003, upper facial rim 1005 and lower facial rim 1006 are shown. In 6A, the facial rims 1005/1006 contact only the incisors, canines and part of cuspids, but not premolars or molars, and thus the bite plate can also accommodate class II/III appliances. However, the facial and lingual rims can be varied in length to contact all, or a portion, of the teeth surfaces, as needed for particular uses.

Also shown in FIG. 6A is the stem 1008, which is the portion of the bite plate 1000 that mates with a corresponding socket in the extraoral housing (not shown here). In more detail, a cylindrical shaft 1009 is shown, having a groove into which a jump ring 1010 fits, and mates with a corresponding depression in the socket. Optional flare 1112 is also shown, and is configured to provide an appropriate surface so that the user can push the stem into the socket.

FIG. 6B shows the inner core of the bite plate, typically made from a resin, such as polycarbonate, metal or ceramic having a harder durometer than the outer surface, and providing sufficient rigidity to the stem 1008 so as to allow it to lockingly fit into the socket. In FIG. 6B, the cylindrical shaft has a groove, into which jump ring or circular coil spring fits. The connector can also having locking pins and/or orientation pins to prevent the bite plate from being inserted upside down. Generally, plastics of at least 40 Shore D are used for the core, but metals or ceramics could also be used. A coating is provided over this core, and provides the final shape of the bite plate, as shown in FIG. 6A. Such coating should be a biocompatible soft polymer of 40-70 Shore A, and particularly preferred is a medical grade, clear silicone.

In addition, it is preferred that the bite plate have a connector that is completely compatible with existing drivers, being of the same size and proportions. Using similar connectors allows the bite plates to be interchangeable, and also allows any bite plate inventory to be used even when the driver unit model is updated. Thus, these sizes are valuable for interchangeability of parts. The minimum for interchangeable parts based on the current models requires the cylindrical post to be about 10.25 mm in length and about 6.35 mm in diameter mm with a groove about 4 mm from the attached end of the post.

The connector in FIG. 6 has a flat surface opposite the bite plate, from which protrudes a centrally positioned cylindrical post that is 6-7 (6.35+0.03, −0.1 tolerances indicated) mm in diameter, 10-11 (10.25) mm in length, and having a groove circumventing the post about half way (4 mm from flat surface, with width of 1.65 mm).

The bottom of the post also has a pair of ~1.4×3 mm pins (optional) projecting 180° from each other (in the same plane as the occlusal contacting base of the bite plate). These pins have a total spread of 11.30 mm at the topmost edge, but flare 10° on each side (20° total) to reach the flat surface of the base. The pins are 1.63 mm thick, and 2.75 mm high.

The base of the connector also preferably has a pair of recessions ~1.5 mm wide×3 mm long×2 mm deep (1.58× 3.27×2.5 mm) on the flat surface thereof for engaging clips from the driver, the recessions being about 16-17 mm apart (22.89 mm in spread), and positioned right below the pins. The recessions can be omitted however, if the base is either not flared or is otherwise smaller, such that the remaining post and pins still fit, leaving the engaging clips on the driver free. These dimensions are approximate, and exact dimensions are provided on FIG. 6.

Markers and Biomarkers

FIG. 7-16 shows various markers and biomarkers that can be used with the diagnostic mouthpads of the invention. Any one or more of the indicated diagnostic indicators can be used herein, preferably, at least 2, 3, 4, 5, 6, 7, 8, 9, 10 diagnostic indicators are used. Obviously, different diagnostic indicators will be selected based on the ease of detection, and the degree of correlation with a disease or predisposition for disease.

We will perform our initial prototyping experiments with markers/biomarkers for oral disease, as these are likely to be of the most immediate interest to dental and orthodontic practitioners. GUSB (β-glucuronidase), for example, can be tested using the substrate phenolphthalein mono-β-glucuronic acid, wherein the product is phenolphthalein (pink above pH 8.2). See U.S. Pat. No. 6,063,588, U.S. Pat. No. 6,277,587.

This can be combined, e.g., with a test strip for e.g., autoinducer 2 (a furanosyl borate diester). Autoinducer 2 can be detected, e.g., with a bioassay using a bacterium which recognizes an autoinducer followed by emitting light, and bacterium such as *Vibrio harveyi* can be spray dried onto the pad for such tests. See e.g., US20120015397, US20120276546, US20100233742. Alternatively, both spot tests and lateral flow tests for 3-glucuronidase can be tested in a prototype device.

Another oral test that is of importance to dental practitioners is one for oral cancer. Therefore, GNAl2 (Guanine Nucleotide-Binding Protein, Alpha-Inhibiting Activity Polypeptide 2) or IFITM3 (Interferon-Induced Transmembrane Protein 3), as examples, may also be tested in the prototype devices. See e.g., US20110236314. Human biomarkers herein are preferably referred to by their HGNC Approved Gene Symbol, but alternative nomenclature can be found at OMIM.org.

Another oral test that may be of importance to parents and employers is one for drugs of abuse or alcohol. Additionally, monitoring of patient compliance with therapeutic drugs can also be tested. FIG. 16 lists the drugs of abuse and therapeutic drugs that are commonly tested for using saliva. Both the drugs and their metabolite can serve as markers.

Each of the following are incorporated by reference herein in their entireties:
US2008227046, US2008227047, US2010055634, US20120322018, US20120040300, US20130059263, 61/624,242 (Apr. 13, 2012), 61/757,288 (Jan. 28, 2013) 61/615,480 (Sep. 14, 2012), 61/673,236 (Jul. 18, 2012); 61/701,532 (Sep. 14, 2012); 61/824,798 (May 17, 2013); 61/837,021 (Jun. 19, 2013).
U.S. Pat. No. 6,648,639, U.S. Pat. No. 6,832,912, U.S. Pat. No. 7,029,276
WO1998029746, US20110236314, US20120322086, US20130022961, US20130017559, US20130022969, U.S. Pat. No. 5,770,460, U.S. Pat. No. 5,798,273, U.S. Pat. No. 6,399,295, U.S. Pat. No. 6,656,744, U.S. Pat. No. 7,344,893, U.S. Pat. No. 7,605,004, U.S. Pat. No. 8,377, 643, U.S. Pat. No. 8,377,710.
Bretz W. A., et al., Systemic inflammatory markers, periodontal diseases, and periodontal infections in an elderly population, J Am Geriatr Soc. 53(9):1532-7 (2005).
Hart, T. C., Microbial and Proteomic Biomarkers in Early Childhood Caries, Intl. J. Dentistry 2011, Article ID 196721, (20111).
Kau, et al., The clinical evaluation of a novel cyclical force generating device in orthodontics, Orthodontic Practice 1(1) (2010).
Kaufman, E., et al., The Diagnostic Applications of Saliva—A Review, Crit. Rev. Oral Biol. Med. 13(2) 2002.
Nordlund, A., et al., Improved ability of biological and previous caries multimarkers to predict caries disease as revealed by multivariate PLS modelling, BMC Oral Health 9:28 (2009).
Pedersen A. N. M., et al., Salivary changes and dental caries as potential oral markers of autoimmune salivary gland dysfunction in primary Sjögren's syndrome, BMC Clinical Pathology 5:4 1472-6890-5-4 (2005)
Rathnayake N., et al., Salivary Biomarkers for Detection of Systemic Diseases, PLoS One. 8(4) (2013).
Ruhl S., The scientific exploration of saliva in the post-proteomic era: from database back to basic function, Expert Rev Proteomics. 9(1):85-96 (2012).
Soo, D., et al., The use of salivary biomarkers in occupational and environmental medicine, Occup Environ Med. 64(3): 202-210 (2007).
US20080183101; US20090047667; US20100196941; US20100233742, US20100210023; US20120028261; US20120276546; US20130065769; WO2007081306; U.S. Pat. No. 6,063,588; U.S. Pat. No. 6,372,513.

While the invention is described above in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A diagnostic pad for oral use, said diagnostic pad comprising:
   i) an absorbent material in a U-shape for contacting occlusal surfaces of dentition;
   ii) said absorbent material comprising at least two diagnostic indicators comprising antibodies for testing at least two salivary markers or biomarkers;
   iii) a transparent flexible waterproof coating on three sides of said absorbent material, leaving one edge open for saliva ingress; and
   iv) an adhesive backing on an outer surface of said coating, said adhesive backing covered with a removable protective layer.

2. A diagnostic pad for oral use, said diagnostic pad comprising:
   i) an absorbent material in a U-shape for contacting occlusal surfaces of dentition;
   ii) said absorbent material comprising at least two diagnostic indicators comprising antibodies for testing at least two salivary markers or biomarkers;
   iii) a transparent flexible waterproof coating on three sides, leaving one edge open for saliva ingress,
   iv) at least one lateral flow immunological test on said diagnostic pad; and
   v) an adhesive backing on an outer bottom surface of said waterproof coating, said adhesive backing covered with a removable protective layer.

3. A diagnostic pad for oral use, said diagnostic pad comprising:
   a) an absorbent material in a rectangular strip having two ends;
   b) said absorbent material comprising at least two diagnostic indicators comprising antibodies for testing at least two salivary markers or biomarkers;
   c) said absorbent material comprising a transparent flexible waterproof coating, leaving at least one open surface for saliva ingress;
   d) said waterproof coating having an adhesive backing on an outer surface, said adhesive backing covered with a removable protective layer; and
   e) having two open edges at each of said two ends, and having a lateral flow immunological test at each of said two ends.

\* \* \* \* \*